(12) United States Patent
Kruger

(10) Patent No.: US 7,648,489 B1
(45) Date of Patent: Jan. 19, 2010

(54) DIAPER CHANGING SYSTEMS

(76) Inventor: Lisa L. Kruger, 14503 N. 152nd Ct., Surprise, AZ (US) 85379

(*) Notice: Subject to any disclaimer, the term of this patent is extended or adjusted under 35 U.S.C. 154(b) by 0 days.

(21) Appl. No.: 11/964,279

(22) Filed: Dec. 26, 2007

Related U.S. Application Data

(60) Provisional application No. 60/882,165, filed on Dec. 27, 2006.

(51) Int. Cl.
*A61F 13/15* (2006.01)
(52) U.S. Cl. ........................................ 604/356; 604/358
(58) Field of Classification Search ......... 604/356–358; D24/124–126
See application file for complete search history.

(56) References Cited

U.S. PATENT DOCUMENTS

| | | | |
|---|---|---|---|
| 1,602,941 A * | 10/1926 | Rosman ........................ | 5/485 |
| 3,406,690 A | 10/1968 | Igel et al. | |
| 3,858,584 A | 1/1975 | Johnson | |
| 3,973,276 A * | 8/1976 | Moses .......................... | 2/215 |
| 4,886,509 A | 12/1989 | Mattsson | |
| 5,706,950 A | 1/1998 | Houghton et al. | |
| 6,009,576 A * | 1/2000 | Gramme et al. ............. | 5/413 R |
| 6,080,139 A | 6/2000 | Gallegos | |
| 6,379,343 B2 | 4/2002 | Stephenson et al. | |
| D491,658 S | 6/2004 | Malcic | |
| 2004/0215105 A1 | 10/2004 | Maples | |
| 2005/0267432 A1 | 12/2005 | Sundberg et al. | |

FOREIGN PATENT DOCUMENTS

GB WO0149151 7/2001

* cited by examiner

*Primary Examiner*—Tatyana Zalukaeva
*Assistant Examiner*—Lynne Anderson
(74) *Attorney, Agent, or Firm*—Stoneman Volk Patent Group; Martin L. Stoneman; Michael D. Volk, Jr.

(57) ABSTRACT

A diaper changing mat comprising an attached, flexible and infant-drapeable, fold-over urine shield structured and arranged to prevent urine exposure from infant-generated urine while still providing easy access to the infant's diaper area. The diaper changing mat is preferably disposable. A preferred heart-shaped urine shield blocks urine streams without hindering access to the infant's diaper area. Alternately preferably, the diaper changing mat may be reusable and washable or preferably comprise a removable waterproof insert. The diaper changing mat may also attach to a changing-table element, such as, for example, a foam pad.

18 Claims, 9 Drawing Sheets

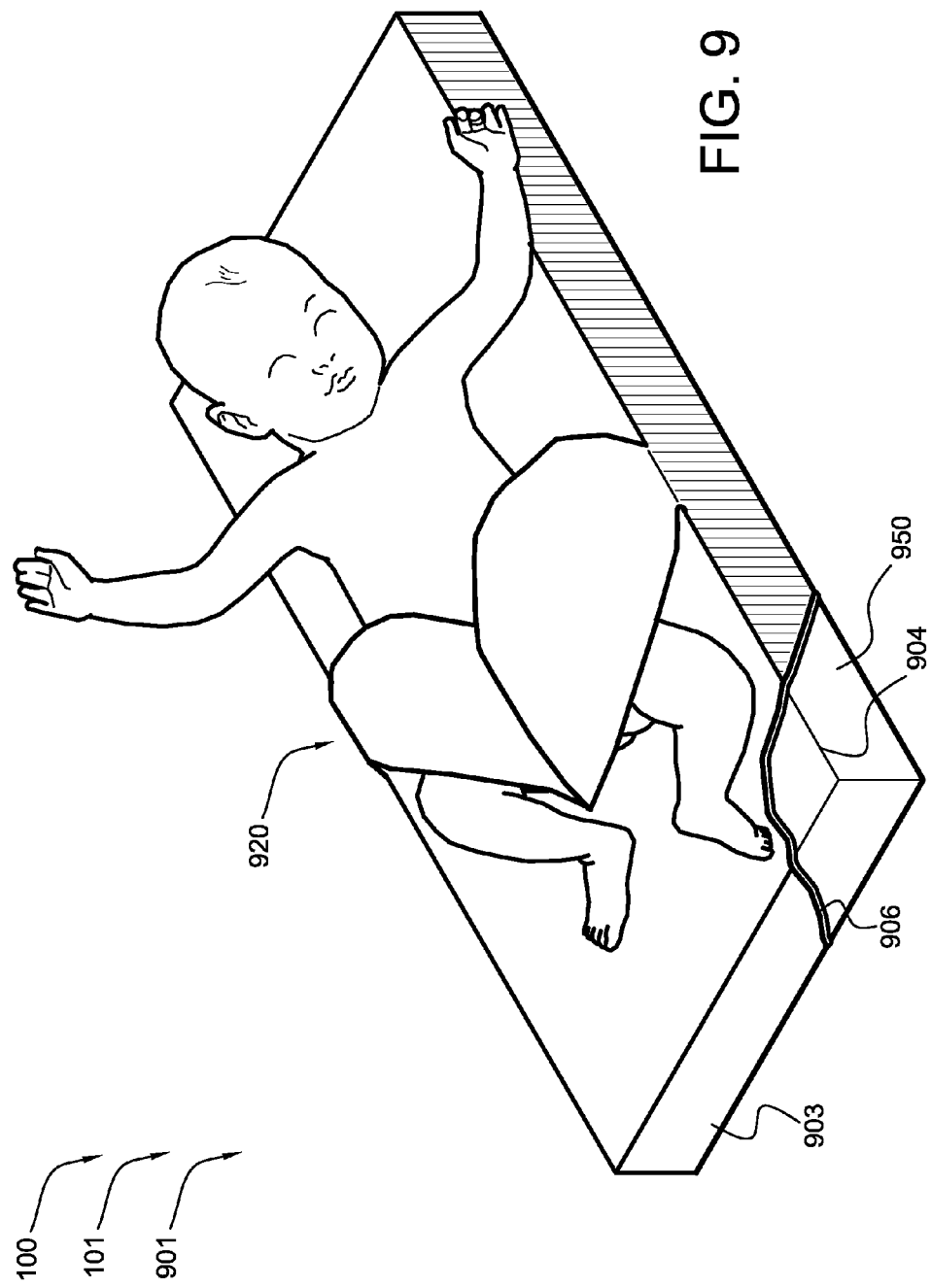

DIAPER CHANGING SYSTEMS

CROSS-REFERENCE TO RELATED APPLICATION

The present application is related to and claims priority from prior provisional application Ser. No. 60/882,165, filed Dec. 27, 2006, entitled "Diaper Changing Systems", the contents of which are incorporated herein by this reference and are not admitted to be prior art with respect to the present invention by the mention in this cross-reference section.

BACKGROUND

The present invention relates to diaper changing systems. More particularly, the present invention relates to diaper changing mats structured and arranged to prevent urine exposure from urine generated by an infant.

When changing a diaper worn by an infant, an infant may spontaneously begin urinating. The urine may potentially contact the person changing the diaper, the infant, the infant's clothing, the diaper-changing surface, and other surroundings, such as, for example, surrounding furniture, carpeting, flooring, items contained in a store or restaurant diaper-changing room, personal belongings, etc. It is undesired and unsanitary to have urine contact the above-mentioned items.

No system exists that provides a diaper changing mat comprising an attached, flexible, and infant-drapeable fold-over urine shield to prevent urine exposure from urine generated by an infant while still providing adequate and easy access to the infant's bottom and diaper-wearing area for diaper-changing purposes. Therefore, a need exists for such a system.

OBJECTS AND FEATURES OF THE INVENTION

A primary object and feature of the present invention is to provide diaper changing systems overcoming the above-mentioned problems and meeting the above-mentioned needs.

It is a further object and feature of the present invention to provide a diaper changing system comprising a diaper-changing mat comprising an attached, flexible, and infant-drapeable fold-over urine shield structured and arranged to prevent and block urine exposure from infant-generated urine while still providing adequate and easy access to the infant's bottom and diaper-wearing area for diaper-changing purposes.

It is still a further object of the present invention to provide such a system that may be disposable.

It is a further object and feature of the present invention to provide such a system comprising a removable waterproof insert. It is another object and feature of the present invention to provide such a system comprising a heart-shaped urine shield that efficiently drapes the lap of an infant.

It is a further object and feature of the present invention to provide such a system that may be reusable.

It is a further object and feature of the present invention to provide such a system that may also attach to a changing-table element.

It is a further object and feature of the present invention to provide such a system that may be used by a person changing a diaper in a variety of environments where accidents involving urine would be unacceptable.

A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a diaper changing system, relating to preventing urine exposure from urine generated by at least one infant while still permitting sufficient access to bottom portions of such at least one infant for diaper-changing purposes by at least one diaper-changer, such diaper changing system comprising: at least one first material layer structured and arranged to lay at least under thigh portions, buttock portions, and lower-back portions of such at least one infant; and at least one second material layer structured and arranged to lay at least over lap portions of such at least one infant; wherein such at least one second material layer comprises portions structured and arranged to drape at least over lap portions of such at least one infant; and at least one connector structured and arranged to connect such at least one first material layer to such at least one second material layer; wherein such at least one second material layer comprises at least one shield structured and arranged to prevent urine exposure from urine generated by such at least one infant; and wherein such at least one first material layer and such at least one second material layer comprise at least one pathway structured and arranged to permit access by such at least one diaper-changer to bottom portions of such at least one infant during diaper-changing.

Moreover, it provides such a diaper changing system, wherein such at least one first material layer and such at least one second material layer each comprise at least one absorber structured and arranged to absorb waste generated by such at least one infant. Additionally, it provides such a diaper changing system, wherein such diaper changing system is disposable after use. Also, it provides such a diaper changing system, wherein such at least one second material layer is structured and arranged to lay over no more than three-fourths the length of such at least one infant. In addition, it provides such a diaper changing system, wherein such at least one connector comprises at least one hinge. And, it provides such a diaper changing system, wherein such at least one hinge is structured and arranged to rotate along an axis approximately parallel to a length of such at least one infant. Further, it provides such a diaper changing system, wherein such at least one connector comprises elastic material.

Even further, it provides such a diaper changing system, wherein such at least one connector comprises at least one slit. Moreover, it provides such a diaper changing system, further comprising at least one changing-table-element connector structured and arranged to connect such at least one first material layer to at least one changing-table element. Additionally, it provides such a diaper changing system, wherein such portions structured and arranged to drape at least over lap portions of such at least one infant comprise at least one first drapeable portion and at least one second drapeable portion; and such at least one first drapeable portion is structured and arranged to drape between the legs of such at least one infant without substantially overlying an adjacent leg of such at least one infant; and such at least one second drapeable portion is structured and arranged to at least partially overlie such at least one first drapeable portion. Also, it provides such a diaper changing system, wherein such at least one first drapeable portion and such at least one second drapeable portion, when overlying, comprise at least one substantially heart-shaped configuration.

In addition, it provides such a diaper changing system, further comprising at least one fluid resister structured and arranged to resist fluid. And, it provides such a diaper changing system, wherein such at least one fluid resister comprises at least one first fluid resister positioned underneath such at least one first material layer, and at least one second fluid resister positioned above such at least one second material layer. Further, it provides such a diaper changing system, wherein such at least one first fluid resister is located within such at least one first material layer; and wherein such at least one second fluid resister is located within such at least one second material layer. Even further, it provides such a diaper changing system, wherein such at least one first fluid resister and such at least one second fluid resister each comprise at least one plastic sheet. Moreover, it provides such a diaper changing system, wherein such at least one first fluid resister and such at least one second fluid resister are removable.

Additionally, it provides such a diaper changing system, wherein such at least one first fluid resister and such at least one second fluid resister are disposable. Also, it provides such a diaper changing system, wherein such at least one first material layer and such at least one second material layer comprise cloth. In addition, it provides such a diaper changing system, wherein such at least one second material layer comprises: at least one first portion; at least one second portion; and at least one releasable fastener structured and arranged to releasably fasten such at least one first portion to such at least one second portion. And, it provides such a diaper changing system, wherein such at least one first material layer comprises at least one first edge and at least one second edge located opposite such at least one first edge; such at least one first portion is connected to such at least one first edge; and such at least one second portion is connected to such at least one second edge. Further, it provides such a diaper changing system, wherein such at least one first material layer and such at least one second material layer comprise at least one releasable fastener structured and arranged to releasably fasten such at least one first material layer to such at least one second material layer.

In accordance with another preferred embodiment hereof, this invention provides a diaper changing system, relating to preventing urine exposure from urine generated by at least one infant while still permitting sufficient access to bottom portions of such at least one infant for diaper-changing purposes by at least one diaper-changer, such diaper changing system comprising: at least one first area comprising at least one top edge, at least one bottom edge, at least one first side edge, and at least one second side edge; and at least one second area comprising at least one third side edge; wherein such at least one third side edge is fixedly connected to such at least one first side edge; wherein the length of such at least one third side edge comprises less than about half the length of such at least one first side edge; wherein such at least one second area comprises less than about half the surface area of such at least one first area; wherein such at least one top edge is between about six inches long and about eighteen inches long; wherein such at least one first side edge is between about twelve inches long and about thirty-six inches long; wherein such at least one first side edge is longer than such at least one top edge; wherein such at least one first area is structured and arranged to lay substantially at least the entire length and the shoulder width of at least one prone infant; wherein such at least one second area is structured and arranged to overlie substantially the entire lap area of such at least one prone infant without overlying the shoulders, head, or feet of such at least one prone infant; wherein such at least one first area comprises fabric; wherein such at least one second area comprises fabric; wherein such at least one first area is structured and arranged to absorb fluid; and wherein such at least one second area is structured and arranged to absorb fluid.

Even further, it provides such a diaper changing system, wherein such at least one second area comprises at least one first portion and at least one second portion; and such diaper changing system comprises at least one releasable fastener structured and arranged to releasably fasten such at least one first portion to such at least one second portion. Even further, it provides such a diaper changing system, further comprising at least one releasable fastener structured and arranged to releasably fasten such at least one second area to such at least one first area.

BRIEF DESCRIPTION OF THE DRAWINGS

FIG. 1A shows a partial close-up view illustrating a preferred material property of the interface between the mat and shield of diaper changing system according to a preferred embodiment of the present invention.

FIG. 1B shows a partial close-up view illustrating a preferred slit arrangement for connector of diaper changing system according to another preferred embodiment of the present invention.

FIG. 9 shows a perspective view illustrating a diaper changing mat, according to the preferred embodiment of the present invention, wherein the diaper changing mat is attached to a changing-table element.

DETAILED DESCRIPTION OF THE BEST MODES AND PREFERRED EMBODIMENTS OF THE INVENTION

Figure 1:
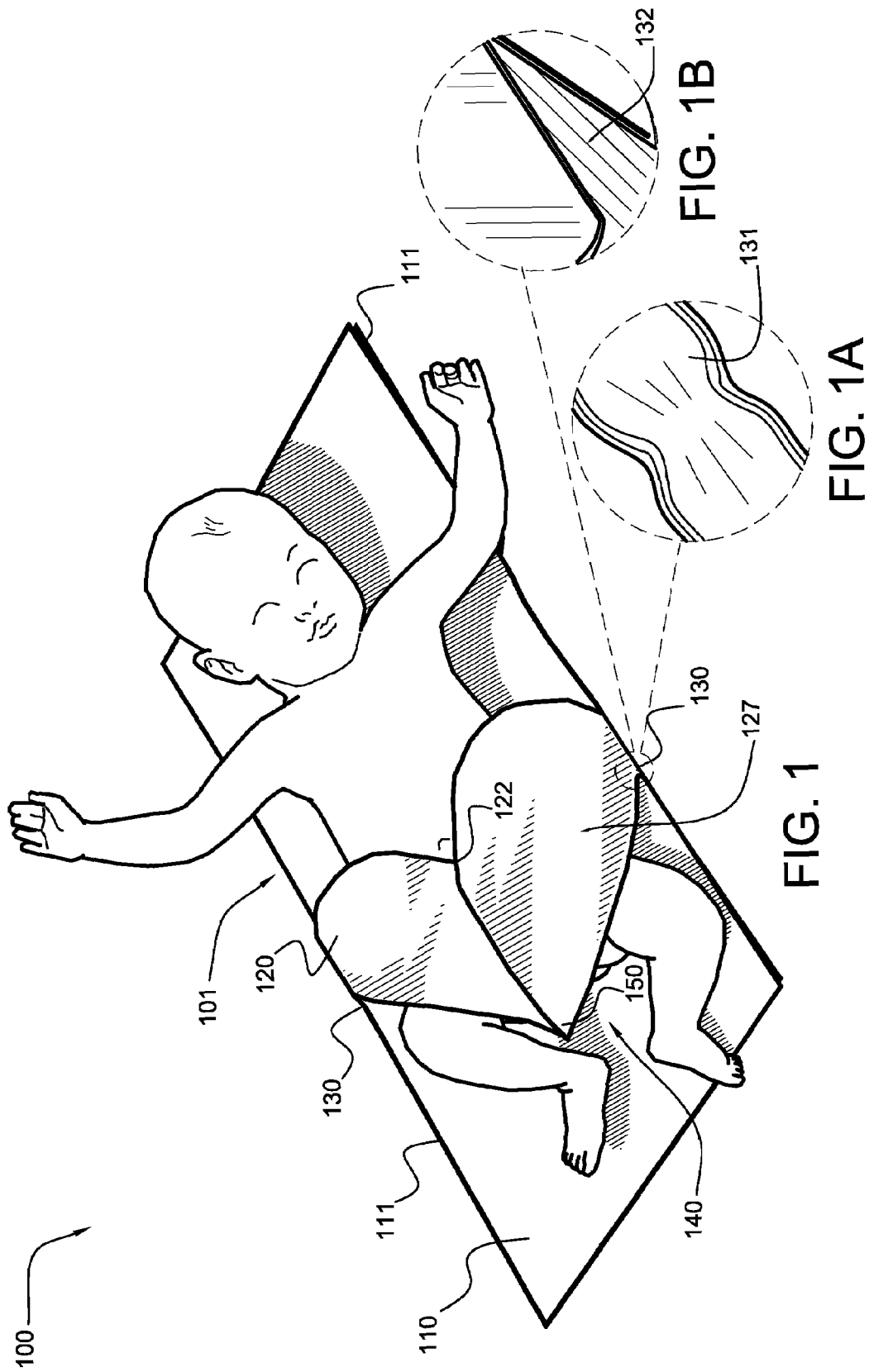
FIG. 1 shows a perspective view illustrating a diaper changing system according to a preferred embodiment of the present invention.

FIG. 1 shows a perspective view illustrating diaper changing system 100 according to a preferred embodiment of the present invention.

Preferably, diaper changing system 100 comprises diaper changing mat 101, as shown. Preferably, diaper changing mat 101 comprises the following preferred components: mat 110, shield 120, connector 130, and accessor 140, as shown. Upon reading the teachings of this specification, those with ordinary skill in the art will now understand that, under appropriate circumstances, considering such issues as advances in technology, user preference, etc., other diaper changing system components, such as safety straps, attachment straps, accessory storage pockets, storage containers, toys, pillows, handles, removable absorbent covers, etc., may suffice. It is highly preferred that diaper changing system 100 be disposable as this provides user convenience with respect to discarding soiled diaper changing system 100. In the event that the diaper changing system 100 is not soiled, a user may preferably reuse diaper changing system 100 accordingly.

Preferably, mat 110 is structured and arranged to lie under at least the legs, the buttocks, and the back of an infant when the infant is laid down on his or her back for a diaper change, as shown. More preferably, mat 110 is structured and arranged to lie under the entire length and width of the infant, as shown. For the purposes of the present patent application, an infant is defined as a human infant typically between about zero and about thirty-six months of age and typically ranging from about eighteen inches to about forty inches in total length.

Preferably, an infant is placed on mat 110 and, subsequently, shield 120 is laid over the infant during-diaper changing procedures (removing a used diaper; cleaning the infant's bottom; applying any powders, ointments, etc.; applying a fresh diaper; etc.), as shown. Preferably, shield 120 is preferably drapeable meaning that, in use, it drapes intended portions of an infant, or is infant-drapeable, as shown (at least embodying herein wherein such at least one second material layer comprises drapeable portions structured and arranged to drape at least over lap portions of such at least one infant). Preferably, shield 120 is flexible, infant-drapeable, and absorbent. Preferably, shield 120 is structured and arranged to lay over no more than about three-fourths the length of a typical infant, as shown, in order to absorb wastes generated by the infant. Such wastes are typically urine, but may also comprise other infant-generated wastes such as feces, other infant-generated body fluids, etc. More preferably, shield 120 is structured and arranged to lie over the lap of the infant, as shown, in order to absorb wastes generated by the infant. For the purposes of the present patent application, the lap is defined as being any portion of the infant substantially between the belly button region and the knee region of the infant on the front side of an infant.

It is common for infants to urinate during diaper-changing when a used diaper is removed. This urine may stream for great distances through the air necessitating clean-up of any urine contacting objects like a parent, the infant, surrounding furniture, personal belongings, etc. Preferably, shield 120 functions to prevent exposure to such urine streams and to prevent such urine streams from leaving the immediate environment of the infant. Shield 120 may also functions to at least partially absorb such urine streams so that the infant is not soaked.

Shield 120 is connected to mat 110 by way of preferred connector 130, as shown. Preferably, connector 130 is structured and arranged to hingedly connect shield 120 to mat 110 along the same axis as the length the infant, as shown. More preferably, connector 130 is structured and arranged to connect shield 120 to mat 110 adjacent the lap of the infant (i.e., adjacent the infant's hips), as shown. Preferably, connector 130 connects shield 120 to the side edges 111 of mat 110, as shown. Preferably, mat 110 and shield 120 are sewn together. More preferably, mat 110 and shield 120 are a single piece of fabric where connector 130 (at least embodying herein at least one connector structured and arranged to connect such at least one first material layer to such at least one second material layer) comprises a living hinge, or fold, defining the connection between mat 110 and shield 120, as shown. Preferably, mat 110 (at least embodying herein (at least embodying herein at least one first material layer structured and arranged to lay at least under thigh portions, buttock portions, and lower-back portions of such at least one infant) and shield 120 (at least embodying herein at least one shield structured and arranged to prevent urine exposure from urine generated by such at least one infant) are connected to each other so that shield 120 does not get lost and so that the infant cannot easily displace or remove shield 120 from over his or her lap when the system is in use. Upon reading the teachings of this specification, those with ordinary skill in the art will now understand that, under appropriate circumstances, considering such issues as advances in technology, user preference, etc., other methods of connecting the mat to the shield, such as the shield being a rigid material attached to the mat with a metal or plastic hinge, etc., may suffice.

FIG. 1A shows a partial close-up view illustrating a preferred material property of the interface between mat 110 and shield 120 of diaper changing system 100 according to a preferred embodiment of the present invention. Preferably, connector 130 comprises elastic material 131. In use, preferred elastic material 131 stretches so that, when a diaper changer lifts an infant's bottom, the bottom of the mat will remain substantially flat against the below-supporting surface. Further, elastic material 131 may also preferably accommodate larger-sized infants. For a larger-sized infant, elastic material 131 is beneficial in that it permits shield 120 to better drape over such larger-sized infant.

FIG. 1B shows a partial close-up view illustrating a preferred slit arrangement for connector 130 of diaper changing system 100 according to another preferred embodiment of the present invention. Connector 130 alternately preferably comprises slit 132 (alternately preferred to elastic material 131), as shown. In use, slit 132 provides a partial opening of connector 130 so that, when a diaper changer lifts an infant's bottom, the bottom of the mat will remain substantially flat against the below-supporting surface. Also, slit 132 may preferably be used to accommodate larger-sized infants.

As stated above, diaper changing system 100 comprises accessor 140, as shown. Accessor 140 is preferably defined by mat 110 and shield 120 as shown. Preferably, accessor 140 permits access to an infant from the diaper-end (feet-end, bottom end, etc.) of an infant during diaper-changing, as shown. In other words, accessor 140 provides a pathway structured and arranged to permit access by a diaper-changer to bottom portions of an infant during diaper-changing. Preferably, accessor 140 is a function of the shape of shield 120 overlying the infant and connected to mat 110 only along the sides of the infant with no obstructions between the infant's legs, as shown. Preferably, a diaper-changer may reach under shield 120 to change the infant-worn diaper with shield 120 in place to block infant-generated urine.

Preferably, diaper changing mat 101 comprises contourer 150 (at least embodying herein wherein said at least one second material layer comprises portions structured and arranged to drape at least over lap portions of such at least one infant) structured and arranged to contour shield 120 so as to preferentially descend between the legs of the infant without substantially overlying the adjacent legs of the infant, as shown. Preferably, shield 120 comprises heart shape 127 giving shield 120 a substantially "heart-shaped" appearance when closed, as shown. Heart-shape 127 of shield 120 (at least embodying herein wherein said first and second drapeable portions, when overlying, comprise at least one substantially heart-shaped configuration) advantageously falls between the infant's legs and blocks urine sprays while helping to maximize the parent's access to the diaper area by avoiding overlying the legs of the infant. Preferably, shield 120 is not attached to mat 110 between the infant's legs, as shown. In addition, heart-shape 127 of shield 120 preferably provides dip 122 (as shown also in FIG. 3) which may help to prevent shield 120 from rubbing against the umbilical cord stumps of newborn infants. Further, heart-shape 127 of shield 120 is aesthetically attractive and is appropriate to infant-care products. Upon reading the teachings of this specification, those with ordinary skill in the art will now understand that, under appropriate circumstances, considering such issues as advances in technology, user preference, etc., other shield shapes, such as loincloth-shaped, round, oval, triangular, square, novelty-shaped, different shapes for boys and girls, etc., may suffice.

Figure 2:
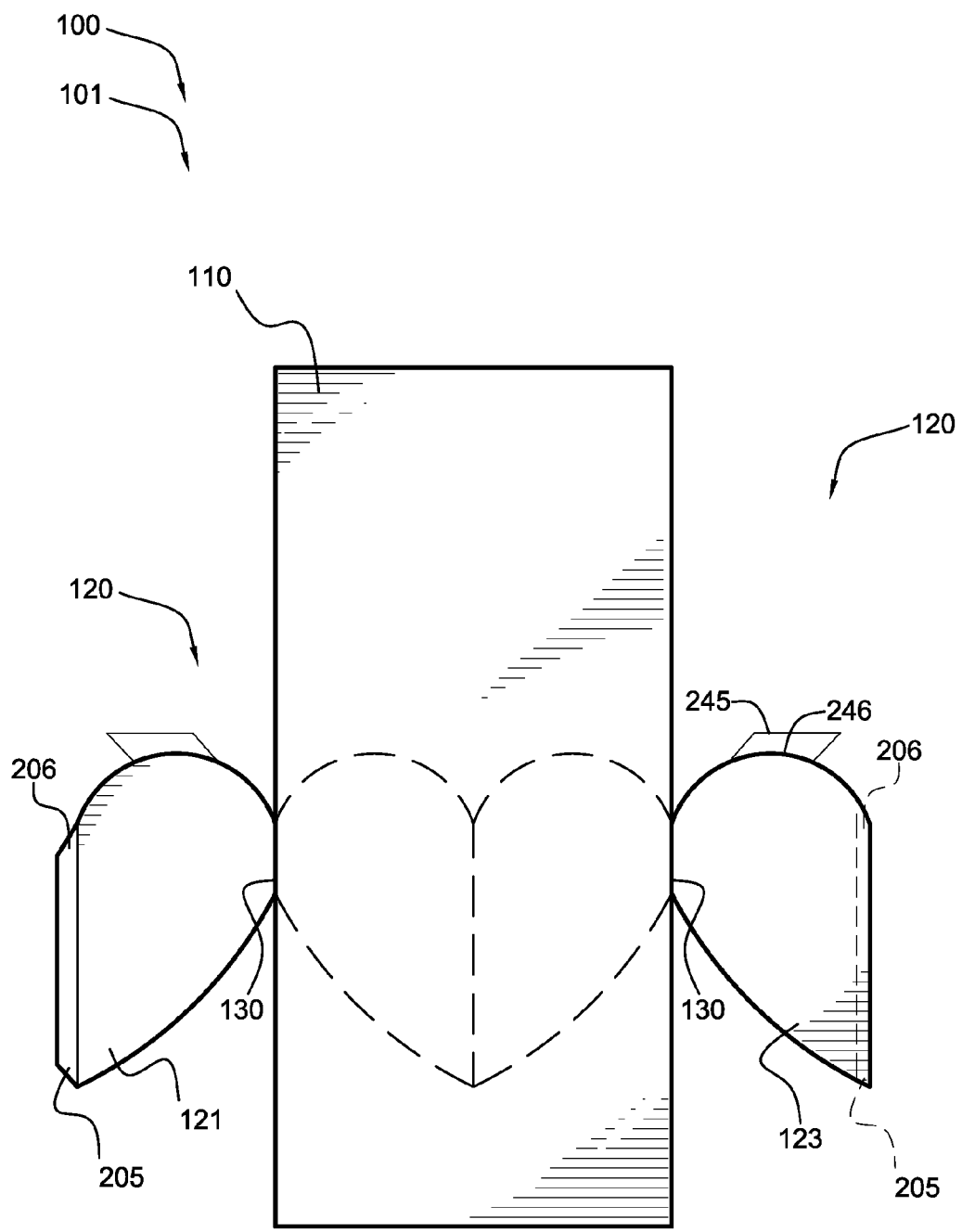
FIG. 2 shows a top view illustrating the diaper changing mat according to the preferred embodiment of FIG. 1, with the shield open.

FIG. 2 shows a top view illustrating diaper changing mat 101 according to the preferred embodiment of FIG. 1, with shield 120 open. Preferably, shield 120 comprises left shield 121 and right shield 123, as shown. Preferably, left shield 121 and right shield 123 comprise releasable fastener 205, as shown. Preferably, releasable fastener 205 (at least embodying herein at least one releasable fastener structured and arranged to releasably fasten said at least one first material layer to said at least one second material layer) permits left shield 121 and right shield 123 to be releasably connected to each other to form one continuous piece in use, as shown in FIG. 1 and in FIG. 3. Preferably, releasable fastener 205 comprises hook and loop fasteners 206, as shown. Upon reading the teachings of this specification, those with ordinary skill in the art will now understand that, under appropriate circumstances, considering such issues as advances in technology, user preference, etc., other fasteners, such as zippers, adhesive, buttons, snaps, etc., may suffice.

Preferably, shield 120 is attached to mat 110 (at least one first material layer structured and arranged to lay at least under thigh portions, buttock portions, and lower-back portions of such at least one infant) adjacent the lap of the infant so that shield 120 (at least embodying herein at least one second material layer structured and arranged to lay at least over lap portions of such at least one infant) folds over the infant's lap in use, as shown in FIG. 1. Preferably, shield 120 is long enough to cross mat 110 and to extend up and over the infant in use, as shown in FIG. 1.

Also, shield 120 may preferably comprise top guard 245, as shown. Top guard 245 is preferably situated along the top portion of shield 120, as shown. Hinge 246 is preferably situated between shield 120 and top guard 245, as shown. In use, top guard 245 preferably "bends" downwardly to the infant via hinge 246 to preferably prevent infant-generated urine from splashing in a direction toward the face of the infant.

Figure 3:
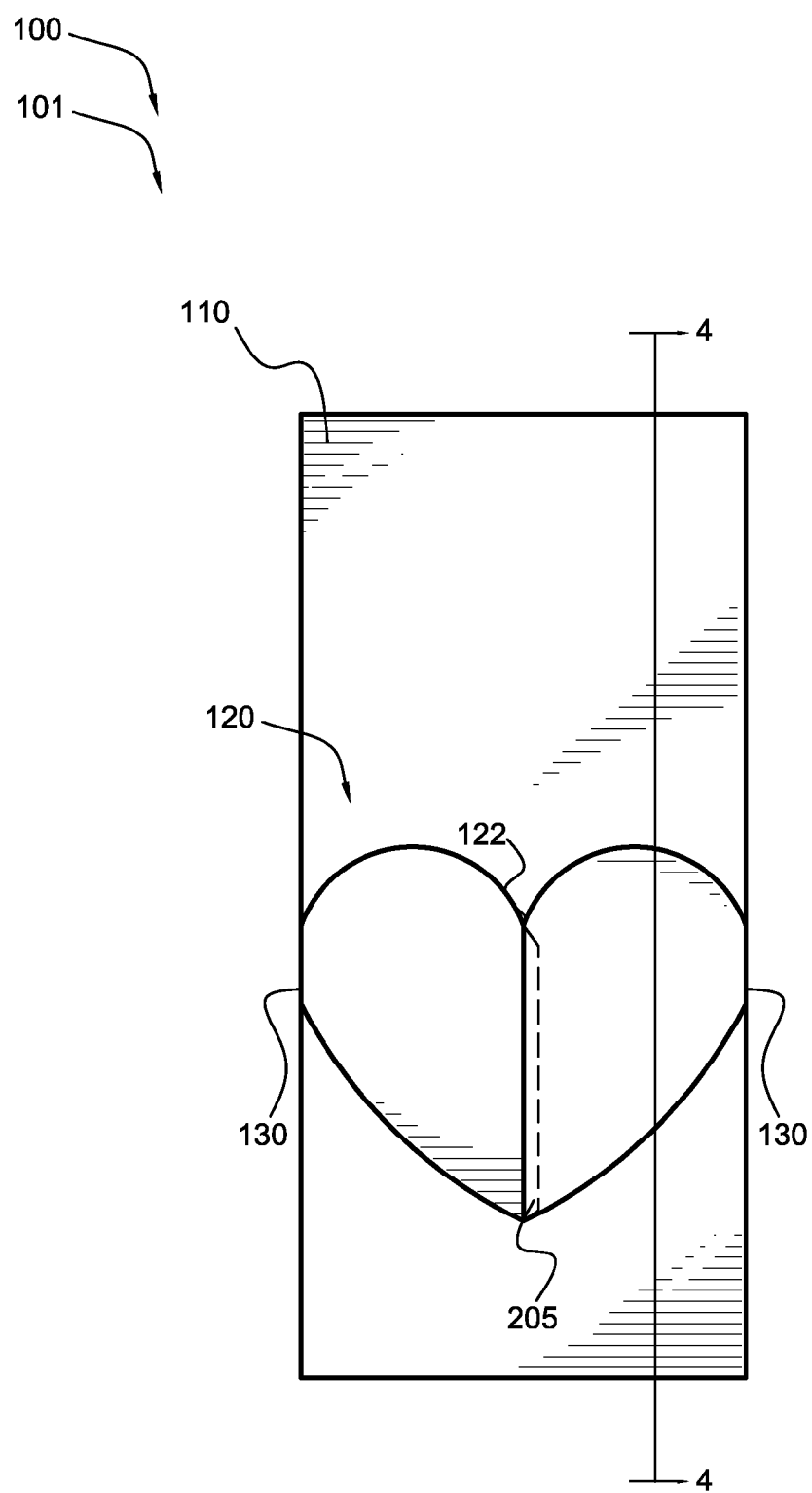
FIG. 3 shows a top view illustrating the diaper changing mat according to the preferred embodiment of FIG. 1, with the shield closed.

FIG. 3 shows a top view illustrating diaper changing mat 101 according to the preferred embodiment of FIG. 1, with shield 120 closed. Preferably, shield 120 is flexible, infant-drapeable, and absorbent. Preferably, shield 120 comprises a disposable material, which may preferably comprise paper or a paper-like material commonly used in disposable diapers, wherein diaper changing mat 101 is disposable. Alternately preferably, shield 120 comprises cloth, wherein diaper changing mat 101 is washable and reusable. In yet another alternative preferred embodiment, shield 120 comprises airlaid fabric wherein diaper changing mat 101 is either disposable or reusable depending on the airlaid material and on user preference. Upon reading the teachings of this specification, those with ordinary skill in the art will now understand that, under appropriate circumstances, considering such issues as advances in technology, user preference, etc., other materials, such as plastic sheets, water-absorbing polymers, padding, etc., may suffice.

Figure 4:
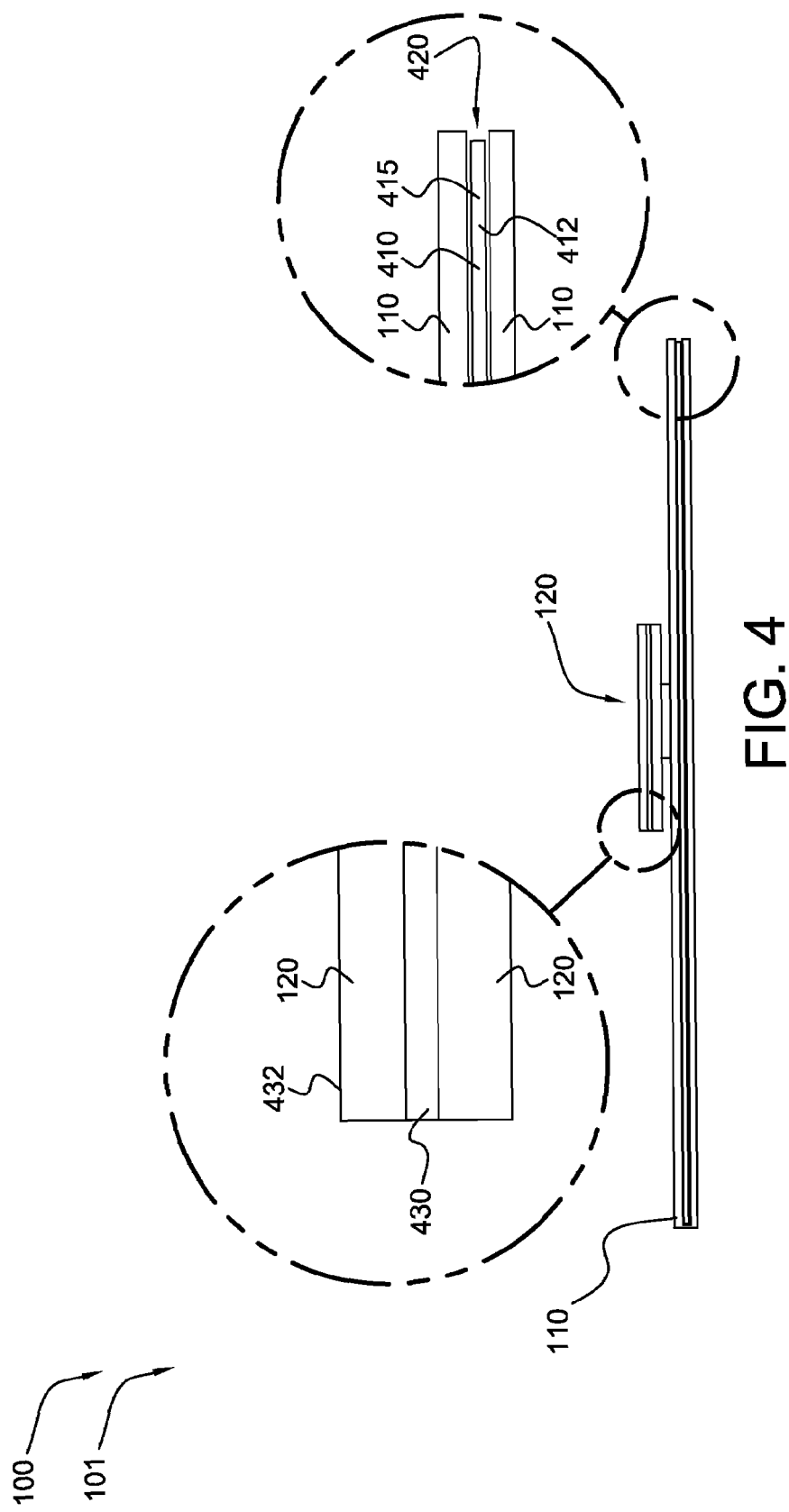
FIG. 4 shows a sectional view illustrating the section 4-4 of FIG. 3.

FIG. 4 shows a sectional view illustrating the section 4-4 of FIG. 3. Preferably, mat 110 comprises waterproof layer 410, as shown. Preferably, waterproof layer 410 waterproofs mat 110 between the infant and the surface underneath mat 110. Preferably, waterproof layer 410 comprises waterproof fabric. Preferably, waterproof layer 410 (at least embodying herein at least one first fluid resister structured and arranged to resist fluid) comprises a plastic sheet. More preferably, waterproof layer 410 comprises plastic waterproof fabric, such as, for example, vinyl, Tyvek™, rubber-impregnated cloth, etc. Upon reading the teachings of this specification, those with ordinary skill in the art will now understand that, under appropriate circumstances, considering such issues as advances in technology, user preference, etc., other water-proof materials, such as water-repellent coatings, oilcloth, leather, etc., may suffice.

Preferably, waterproof layer 410 may comprise removable waterproof layer 415, as shown. Preferably, removable waterproof layer 415 (at least embodying herein wherein said at least one first fluid resister is removable) is located within mat 110, as shown. Preferably, removable waterproof layer 415 is removable from mat 110 through opening 420, as shown. Preferably, removable waterproof layer 415 comprises at least one semi-rigid plastic sheet 412, as shown. Preferably, semi-rigid plastic sheet 412 (at least embodying herein wherein such at least one removable fluid-resister comprises at least one semi-rigid plastic sheet) provides shape and structure to mat 110 while being flexible enough to be rolled up and/or folded for portability.

Preferably, shield 120 comprises waterproof layer 430, as shown. Preferably, waterproof layer 430 waterproofs shield 120 between the infant and top side 432 of shield 120. Preferably, waterproof layer 430 keeps top side 432 dry so that shield 120 does not get the parent's hands wet as shield 120 is being opened or moved after use. Preferably, waterproof layer 430 comprises a plastic sheet. More preferably, waterproof layer 430 comprises plastic waterproof fabric, such as, for example, vinyl, Tyvek™, rubber-impregnated cloth, etc. Upon reading the teachings of this specification, those with ordinary skill in the art will now understand that, under appropriate circumstances, considering such issues as advances in technology, user preference, etc., other water-proof materials, such as water-repellent coatings, oilcloth, leather, etc., may suffice.

Figure 5:
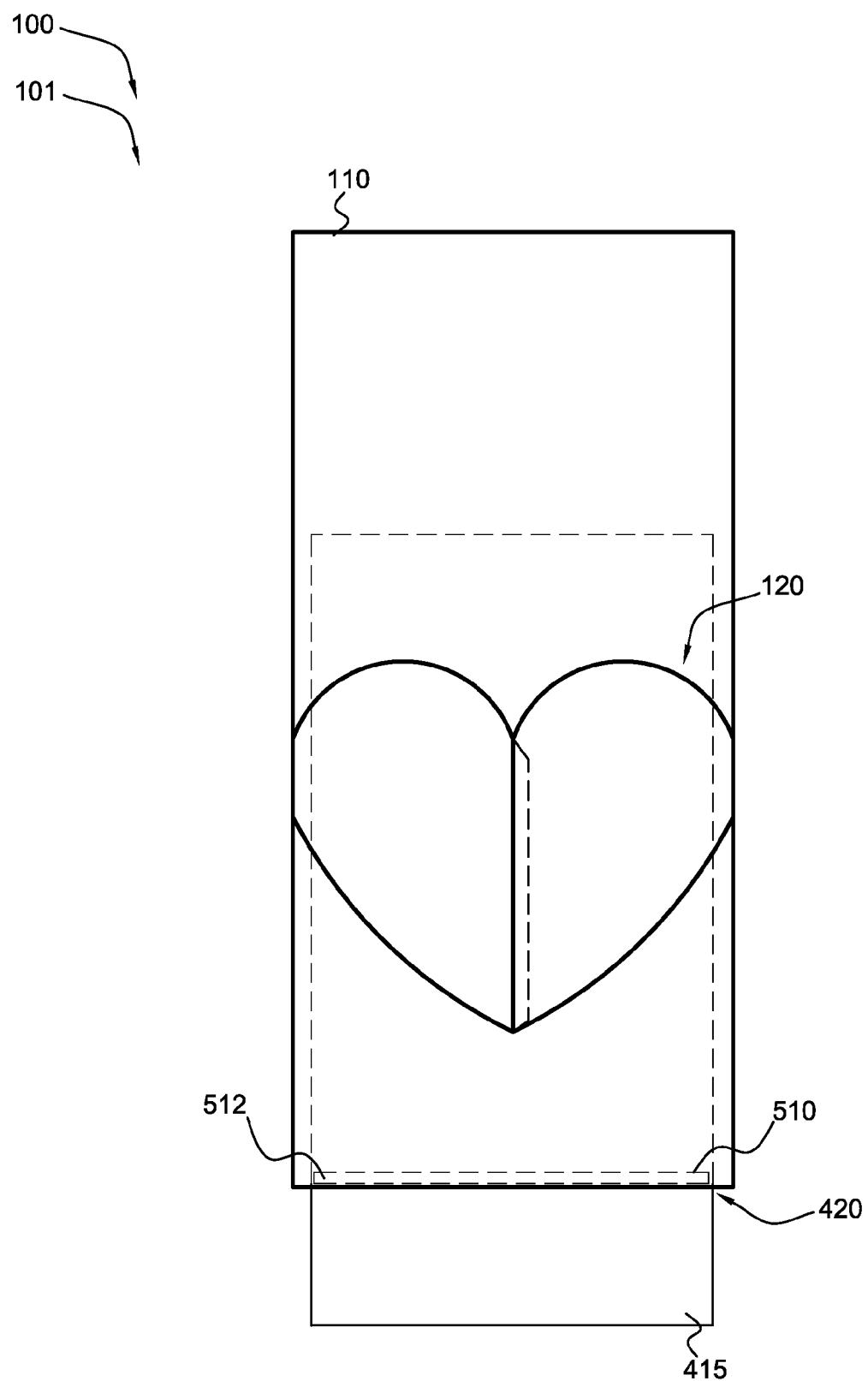
FIG. 5 shows a top view illustrating a diaper changing mat according to another preferred embodiment of the present invention, particularly illustrating removal of a removable fluid resister.

FIG. 5 shows a top view illustrating diaper changing mat 101 according to the preferred embodiment of FIG. 1, during removal of removable waterproof layer 415. Preferably, removable waterproof layer 415 is removable, as shown, so that diaper changing mat 101 can be easily laundered. It is generally not preferred to run semi-rigid plastic sheets through laundry washing machines because of mechanical and/or heat damage that may result.

Preferably, opening 420 comprises openable fastener 510, as shown. Preferably, openable fastener 510 comprises hook and loop fasteners 512, as shown. Upon reading the teachings of this specification, those with ordinary skill in the art will now understand that, under appropriate circumstances, considering such issues as advances in technology, user preference, etc., other fasteners, such as zippers, adhesive, buttons, snaps, etc., may suffice.

Figure 6:
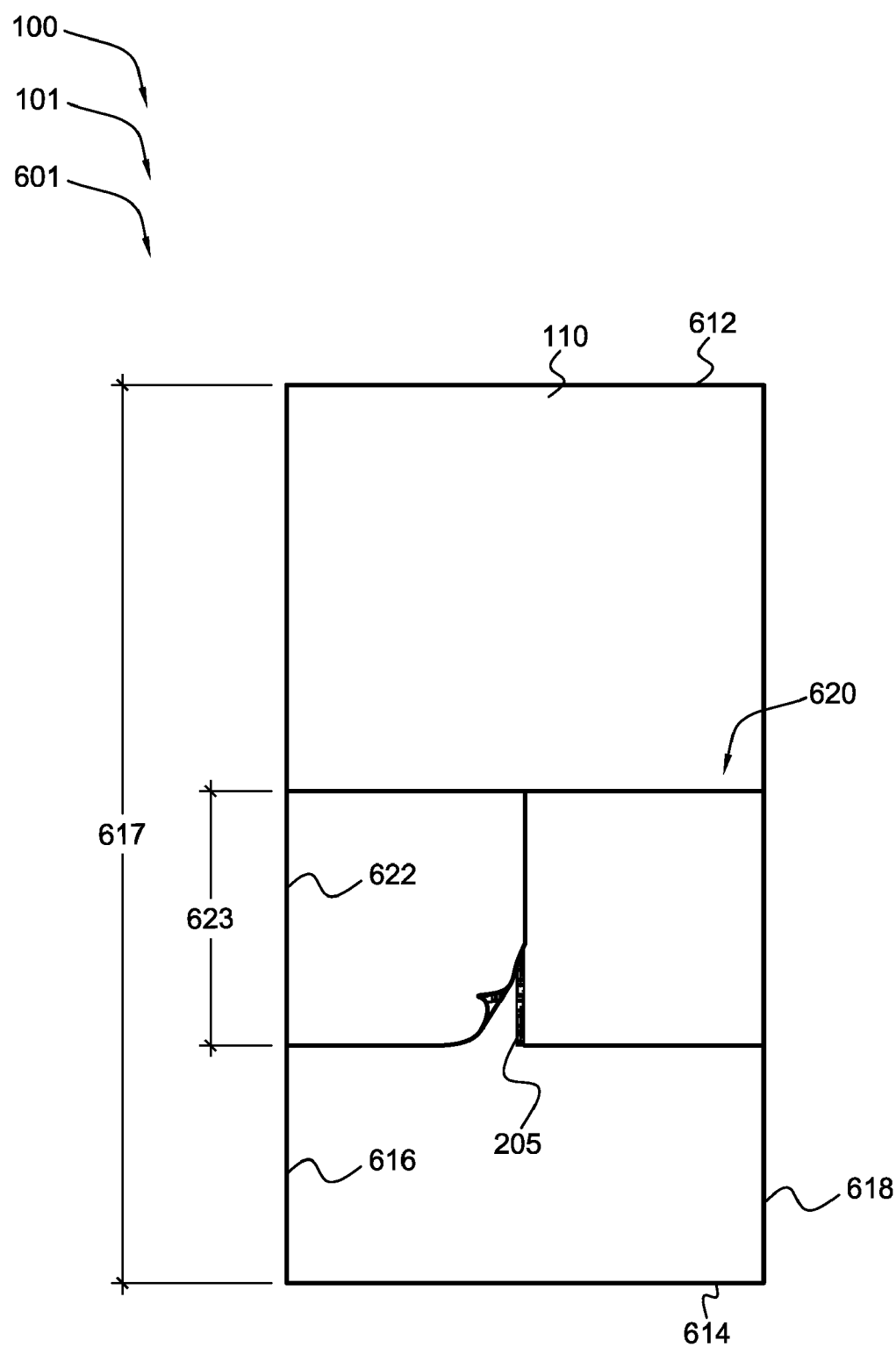
FIG. 6 shows a top view illustrating a diaper changing mat, according to a preferred embodiment of the present invention, having a two-part rectangular shield.

FIG. 6 shows a top view illustrating diaper changing mat 601 according to a preferred embodiment of the present invention, having a two-part rectangular shield 620.

Preferably, diaper changing mat 101 comprises diaper changing mat 601, as shown. Preferably, diaper changing mat 601 is a modification of diaper changing mat 101, as shown. Preferably, shield 120 comprises shield 620, as shown. Preferably, shield 620 is substantially rectangular when closed, as shown.

Preferably, diaper changing mat 601 comprises mat 110 and shield 620, as shown. Preferably, mat 110 (at least embodying herein at least one first area comprising at least one top edge, at least one bottom edge, at least one first side edge, and at least one second side edge) comprises at least one top edge 612, at least one bottom edge 614, at least one first side edge 616, and at least one second side edge 618, as shown. Preferably, shield 620 (at least embodying herein at least one second area comprising at least one third side edge) comprises at least one third side edge 622, as shown.

Preferably, third side edge 622 is fixedly connected to first side edge 616, as shown (at least embodying herein wherein such at least one third side edge is fixedly connected to such at least one first side edge). Preferably, length 623 of third side edge 622 comprises less than about half length 617 of first side edge 616, as shown (at least embodying herein wherein the length of such at least one third side edge comprises less than about half the length of such at least one first side edge). Preferably, shield 620 comprises less than about half the surface area of mat 110, as shown (at least embodying herein wherein such at least one second area comprises less than about half the surface area of such at least one first area).

Preferably, first top edge 612 is between about six inches long and about eighteen inches long. Preferably, first side edge 616 is between about twelve inches long and about thirty-six inches long. Preferably, first side edge 616 is longer than top edge 612, as shown.

Preferably, mat 110 is structured and arranged to underlie substantially at least the entire length and the shoulder width of the prone infant, as shown in FIG. 1 (at least embodying herein wherein such at least one first area is structured and arranged to underlie substantially at least the entire length and the shoulder width of at least one prone infant). Preferably, shield 620 is structured and arranged to overlie substantially the entire lap area of the prone infant without overlying the shoulders, head, or feet of the prone infant, substantially as shown in FIG. 1 (at least embodying herein wherein such at least one second area is structured and arranged to overlie substantially the entire lap area of such at least one prone infant without overlying the shoulders, head, or feet of such at least one prone infant). Preferably, mat 110 comprises fabric (at least embodying herein wherein such at least one first area comprises fabric). Preferably, mat 110 is water-absorbent (at least embodying herein wherein such at least one first area is structured and arranged to resist fluid). Preferably, shield 620 comprises fabric (at least embodying herein wherein such at least one second area comprises fabric). Preferably, shield 620 is water-absorbent (at least embodying herein wherein such at least one second area is structured and arranged to resist fluid). Preferably, shield 620 comprises releasable fastener 205, as shown. Upon reading the teachings of this specification, those with ordinary skill in the art will now understand that, under appropriate circumstances, considering such issues as advances in technology, user preference, etc., other mat shapes, such as round, oval, novelty-shaped, square cross-shaped, etc., may suffice.

Figure 7:
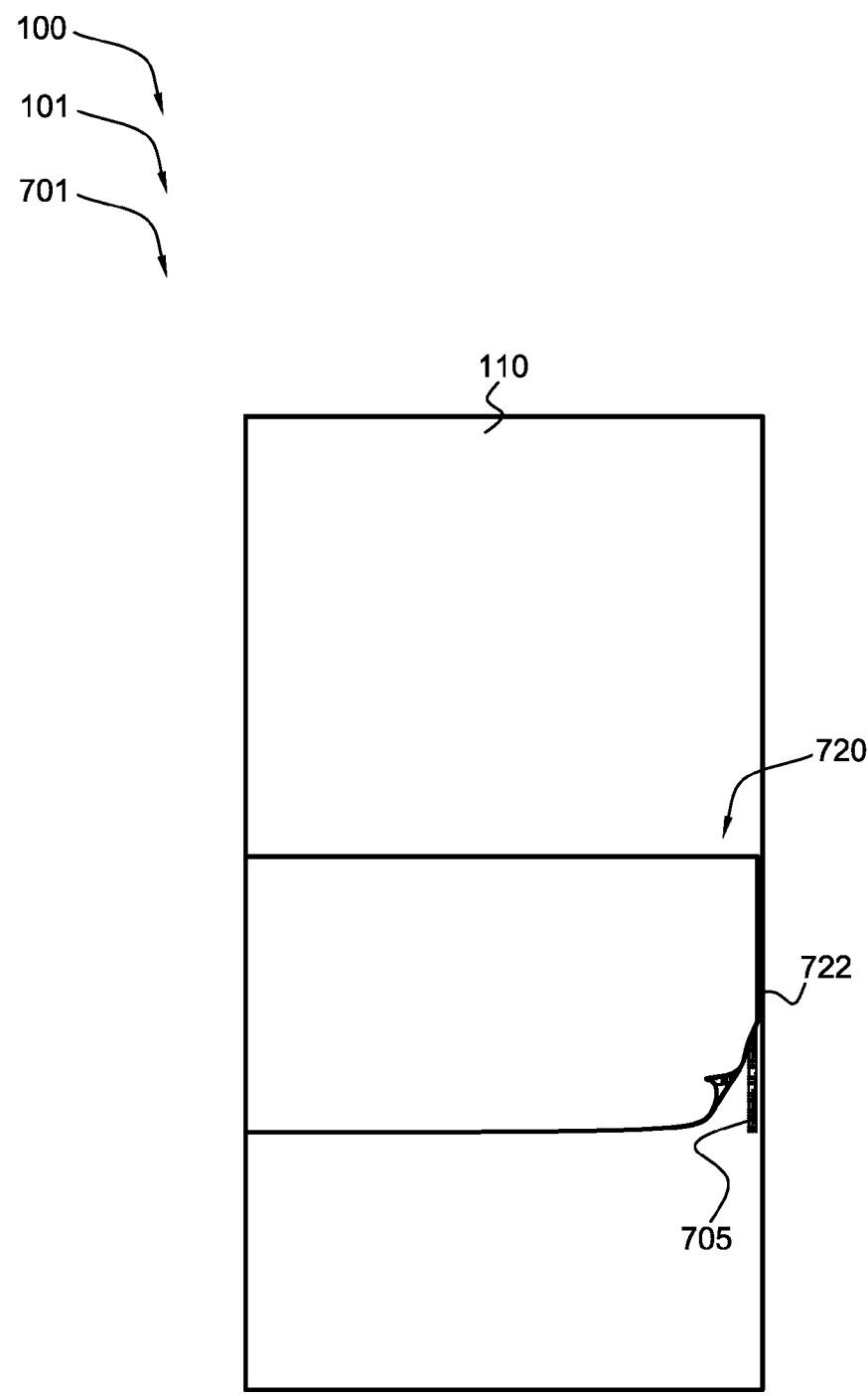
FIG. 7 shows a top view illustrating a diaper changing mat, according to a preferred embodiment of the present invention, having a one-piece rectangular shield.

FIG. 7 shows a top view illustrating diaper changing mat 701 according to the preferred embodiment of the present invention, having a one-piece rectangular shield 720.

Preferably, diaper changing mat 101 comprises diaper changing mat 701, as shown. Preferably, diaper changing mat 701 is a modification of diaper changing mat 101, as shown. Preferably, shield 120 comprises shield 720, as shown. Preferably, shield 720 is substantially rectangular, as shown.

Preferably, shield 720 is structured and arranged to overlie substantially the entire lap area of the prone infant without overlying the shoulders, head, or feet of the prone infant, substantially as shown in FIG. 1. Preferably, releasable fastener 205 comprises releasable fastener 705, as shown. Preferably, releasable fastener 705 releasably fastens the free end 722 of shield 720 to mat 110, as shown.

Figure 8:
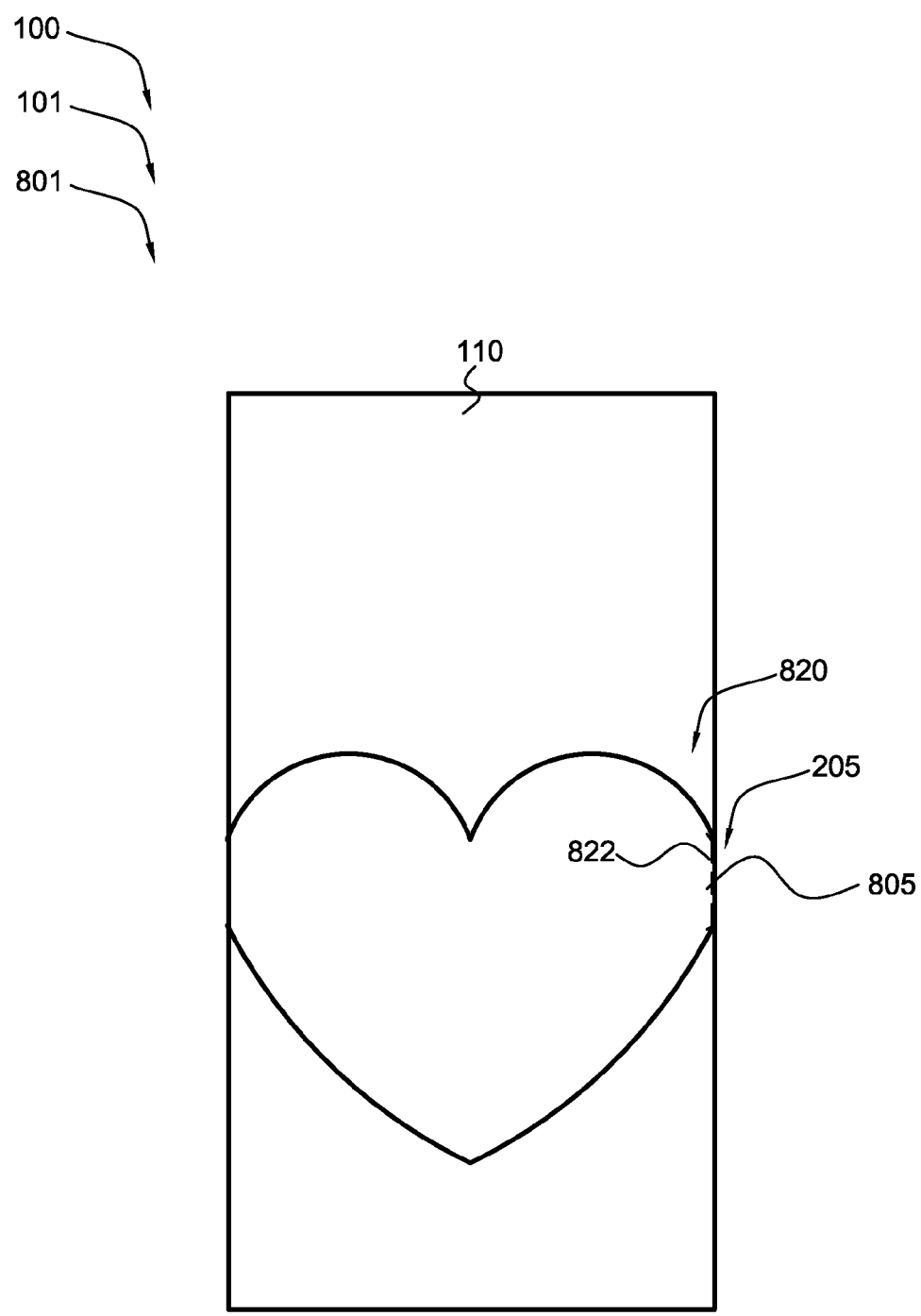
FIG. 8 shows a top view illustrating a diaper changing mat, according to a preferred embodiment of the present invention, having a one-piece heart-shaped shield.

FIG. 8 shows a top view illustrating diaper changing mat 801 according to a preferred embodiment of the present invention, having a one-piece heart-shaped shield 820.

Preferably, diaper changing mat 101 comprises diaper changing mat 801, as shown. Preferably, diaper changing mat 801 is a modification of diaper changing mat 101, as shown. Preferably, shield 120 (at least embodying herein at least one second material layer structured and arranged to lay at least over lap portions of such at least one infant) comprises shield 820, as shown.

Preferably, shield 820 is structured and arranged to overlie substantially the entire lap area of the prone infant without overlying the shoulders, head, or feet of the prone infant, substantially as shown in FIG. 1. Preferably, releasable fastener 205 comprises releasable fastener 805, as shown. Preferably, releasable fastener 805 (at least embodying herein wherein said at least one first material layer and said at least one second material layer comprise at least one releasable fastener structured and arranged to releasably fasten said at least one first material layer to said at least one second material layer) releasably fastens the free end 822 of shield 820 to mat 110, as shown.

FIG. 9 shows a perspective view illustrating diaper changing mat 901 according to the preferred embodiment of the present invention, wherein shield 920 is attached to changing-table element cover 903.

Preferably, diaper changing mat 101 comprises diaper changing mat 901, as shown. Preferably, diaper changing mat 901 is a modification of diaper changing mat 101, as shown. Preferably, mat 110 comprises changing-table element cover 903, as shown. Preferably, changing-table element cover 903 removably connects to at least one changing-table element 950, as shown. Preferably, changing-table element cover 903 comprises a fitted fabric sheet structured and arranged fit changing-table element 950, as shown. Preferably, changing-table element cover 903 (at least embodying herein at least one table-connector structured and arranged to connect said at least one first material layer to at least one changing-table element) comprises elastic 906, as shown. Typically, changing-table element 950 comprises a foam pad.

Preferably, shield 920 is connected (preferably sewn) to changing-table element cover 903 such that shield 920 extends from changing-table element cover 903 adjacent top edges 904 of changing-table element 950, as shown. Upon reading the teachings of this specification, those with ordinary skill in the art will now understand that, under appropriate circumstances, considering such issues as advances in technology, user preference, etc., other arrangements, such as the shield being attached to the changing table, etc., may suffice.

Although applicant has described applicant's preferred embodiments of this invention, it will be understood that the broadest scope of this invention includes modifications such as diverse shapes, sizes, and materials. Such scope is limited only by the below claims as read in connection with the above specification. Further, many other advantages of applicant's invention will be apparent to those skilled in the art from the above descriptions and the below claims.

What is claimed is:

1. A diaper changing system, relating to preventing urine exposure from urine generated by at least one infant while still permitting sufficient access to bottom portions of such at least one infant for diaper-changing purposes by at least one diaper-changer, said diaper changing system comprising:
- a) at least one mat structured and arranged to lay at least under thigh portions, buttock portions, and back portions of such at least one infant;
- b) said at least one mat having
  - i) a top, a bottom, and an outer periphery, and
  - ii) an upper portion and a lower portion of essentially equal dimensions, said upper portion and said lower portion essentially separated by a first line passing through the midpoint of a second line extending from said top to said bottom, said first line being perpendicular to said second line;
- c) at least one shield structured and arranged to lay over only the lap portion of such at least one infant by being predominantly positioned below said first line;
- d) wherein said at least one shield comprises portions structured and arranged to drape over the lap portion of such at least one infant; and
- e) at least one connector structured and arranged to connect said at least one mat to said at least one shield;
- f) wherein said at least one connector is positioned at said outer periphery of said at least one mat;
- g) at least one slit positioned adjacent the connection point of said at least one connector, said at least one slit permitting raising and lowering of said at least one shield relative to said at least one mat;
- h) wherein said at least one shield is structured and arranged to prevent urine exposure from urine generated by such at least one infant; and
- i) wherein said at least one mat and said at least one shield comprise at least one pathway structured and arranged to permit access by such at least one diaper-changer to bottom portions of such at least one infant during diaper-changing.

2. The diaper changing system, according to claim 1, wherein said at least one mat and said at least one shield are absorbent to absorb waste generated by such at least one infant.

3. The diaper changing system, according to claim 2, wherein said diaper changing system is disposable after use.

4. The diaper changing system, according to claim 2, wherein said at least one connector comprises at least one hinge.

5. The diaper changing system, according to claim 4, wherein said at least one hinge is structured and arranged to rotate along an axis approximately parallel to said second line.

6. The diaper changing system, according to claim 2, further comprising at least one changing-table-element connector structured and arranged to connect said at least one mat to at least one changing-table element.

7. The diaper changing system, according to claim 2, wherein
- a) said portions structured and arranged to drape at least over lap portions of such at least one infant comprise at least one first drapeable portion and at least one second drapeable portion; and
- b) said at least one first drapeable portion is structured and arranged to drape between the legs of such at least one infant without substantially overlying an adjacent leg of such at least one infant; and
- c) said at least one second drapeable portion is structured and arranged to at least partially overlie said at least one first drapeable portion.

8. The diaper changing system, according to claim 7, wherein said at least one first drapeable portion and said at least one second drapeable portion, when overlying, resemble at least one stylized heart shape, an upper portion of which resembles a cardioid curve having at least one cusp, wherein the at least one cusp of the cardioid curve defines a void to avoid contact of said at least one shield with the navel area of such at least one infant.

9. The diaper changing system, according to claim 2, further comprising at least one fluid resister structured and arranged to resist fluid.

10. The diaper changing system, according to claim 9, wherein said at least one fluid resister comprises
- a) at least one first fluid resister positioned underneath said at least one mat, and
- b) at least one second fluid resister positioned above said at least one shield.

11. The diaper changing system, according to claim 10, wherein said at least one first fluid resister is located within said at least one mat; and wherein said at least one second fluid resister is located within said at least one shield.

12. The diaper changing system, according to claim 11, wherein said at least one first fluid resister and said at least one second fluid resister each comprise at least one plastic sheet.

13. The diaper changing system, according to claim 11, wherein said at least one first fluid resister and said at least one second fluid resister are removable.

14. The diaper changing system, according to claim 11, wherein said at least one first fluid resister and said at least one second fluid resister are disposable.

15. The diaper changing system, according to claim 2, wherein said at least one mat and said at least one shield comprise cloth.

16. The diaper changing system, according to claim 1, wherein said at least one shield comprises:
- a) at least one first portion;
- b) at least one second portion; and
- c) at least one releasable fastener structured and arranged to releasably fasten said at least one first portion to said at least one second portion.

17. The diaper changing system, according to claim 1, wherein said at least one mat and said at least one shield comprise at least one releasable fastener structured and arranged to releasably fasten said at least one mat to said at least one shield.

18. A diaper changing system, relating to preventing urine exposure from urine generated by at least one infant while still permitting sufficient access to bottom portions of such at least one infant for diaper-changing purposes by at least one diaper-changer, said diaper changing system comprising:
- a) at least one mat structured and arranged to lay at least under thigh portions, buttock portions, and back portions of such at least one infant;
- b) said at least one mat having
  - i) a top, a bottom, and an outer periphery, and
  - ii) an upper portion and a lower portion of essentially equal dimensions, said upper portion and said lower portion essentially separated by a first line passing through the midpoint of a second line extending from said top to said bottom, said first line being perpendicular to said second line;
- c) at least one shield structured and arranged to lay over only the lap portion of such at least one infant by being predominantly positioned below said first line;
- d) wherein said at least one shield comprises portions structured and arranged to drape over the lap portion of such at least one infant; and
- e) at least one connector structured and arranged to connect said at least one mat to said at least one shield;

f) wherein said at least one connector is positioned at said outer periphery of said at least one mat;
g) wherein said at least one shield comprises at least one shield structured and arranged to prevent urine exposure from urine generated by such at least one infant;
h) wherein said at least one mat and said at least one shield comprise at least one pathway structured and arranged to permit access by such at least one diaper-changer to bottom portions of such at least one infant during diaper-changing;
i) wherein said at least one shield resembles at least one stylized heart shape, an upper portion of which resembles a cardioid curve having at least one cusp, wherein the at least one cusp of the cardioid curve defines a void to avoid contact of said at least one shield with the navel area of such at least one infant.

* * * * *